United States Patent
Annereau et al.

(10) Patent No.: US 11,730,732 B2
(45) Date of Patent: Aug. 22, 2023

(54) ORAL SUSPENSION OF TEMOZOLOMIDE

(71) Applicants: Orphelia Pharma, Paris (FR); Institut Gustave Roussy, Villejuif (FR)

(72) Inventors: Maxime Annereau, Vincennes (FR); Jérémy Bastid, Tassin La Demi Lune (FR); Hugues Bienaymé, Saint-Symphorien-d'Ozon (FR); François Lemare, Suresnes (FR); Mathieu Schmitt, Paris (FR); Lionel Tortolano, Paris (FR); Samuel Abbou, Paris (FR)

(73) Assignees: Orphelia Pharma, Paris (FR); Institut Gustave Roussy, Villejuif (FR)

(\*) Notice: Subject to any disclaimer, the term of this patent is extended or adjusted under 35 U.S.C. 154(b) by 140 days.

(21) Appl. No.: 16/713,096

(22) Filed: Dec. 13, 2019

(65) Prior Publication Data

US 2020/0188390 A1 Jun. 18, 2020

(30) Foreign Application Priority Data

Dec. 13, 2018 (EP) .................................... 18306683

(51) Int. Cl.
| | | |
|---|---|---|
| *A61K 31/495* | (2006.01) | |
| *A61K 9/08* | (2006.01) | |
| *A61K 47/02* | (2006.01) | |
| *A61K 47/10* | (2017.01) | |
| *A61K 47/12* | (2006.01) | |
| *A61K 47/32* | (2006.01) | |
| *A61K 47/38* | (2006.01) | |
| *A61K 47/40* | (2006.01) | |
| *A61K 9/00* | (2006.01) | |

(52) U.S. Cl.
CPC .............. *A61K 31/495* (2013.01); *A61K 9/08* (2013.01); *A61K 47/02* (2013.01); *A61K 47/10* (2013.01); *A61K 47/12* (2013.01); *A61K 47/32* (2013.01); *A61K 47/38* (2013.01); *A61K 47/40* (2013.01); *A61K 9/0053* (2013.01)

(58) Field of Classification Search
CPC ...... A61K 9/08; A61K 9/0053; A61K 31/495; A61K 47/02; A61K 47/10; A61K 47/12; A61K 47/32; A61K 47/38; A61K 47/40; A61K 47/36; A61K 9/0095
See application file for complete search history.

(56) References Cited

U.S. PATENT DOCUMENTS

2005/0187206 A1  8/2005 Adin et al.

FOREIGN PATENT DOCUMENTS

| WO | WO 2008/111092 | 9/2008 |
|---|---|---|
| WO | WO 2008/167627 | 9/2018 |
| WO | WO 2018/200034 | 11/2018 |

OTHER PUBLICATIONS

Trissel et al. Inter J Pharm Compouding. 2006; 10(5): 396-399. (Year: 2006).*
Anonymous. Inter J Pharm Compounding. 2007; 11(4): 336. (Year: 2007).*
Dash. Pharmatutor [online]; 2011; downloaded from <URL https://www.pharmatutor.org/articles/effect-of-particle-size-on-stability-of-suspension > on Nov. 4, 2021; 6 pages. (Year: 2011).*
European Search Report and the European Search Opinion dated Jun. 13, 2019 From the European Patent Office Re. Application No. 18306683.6. (13 Pages).
Ambados et al. "Preparation Method and Stability of A Temozolomide Suspension: A Pilot Study", Journal of Pharmacy Practice and Reasearch, XP055365602, 42(2): 111-114, Published Online Jun. 1, 2012.
Anonymus "Temozolomide 10-mg/mL Oral Liquid", International Journal of Pharmaceutical Compounding, XP009501878, 11(4): 336, Jul./Aug. 2007.
Merck Sharp & Dohme "Annex I Summary of Product Characteristics: Temodal 5mg Hard Capsules", Retrieved From the Internet, XP055595194, Product Information, p. 1-188, Sep. 3, 2018.
Schering "Temodar® (Temozolomide) Capsules", Schering Corporation, XP002460101, Product Information, 4 P., Nov. 2006.
Trissel et al. "Temozolomide Stability in Extemporaneously Compounded Oral Suspensions", International Journal of Pharmaceutical Compounding, XP009501881, 10(5): 396-399, Sep./Oct. 2006.

\* cited by examiner

*Primary Examiner* — David Browe

(57) ABSTRACT

A pharmaceutical liquid suspension comprising: temozolomide or a salt thereof; at least one agent controlling the solid state of temozolomide in suspension; a pharmaceutically acceptable liquid vehicle; and optionally at least one acid in a quantity so that the pH of the composition is below 5; or a powder blend for reconstituting said suspension, is provided.

16 Claims, 9 Drawing Sheets

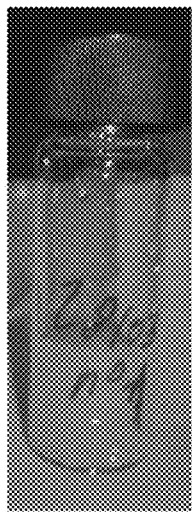 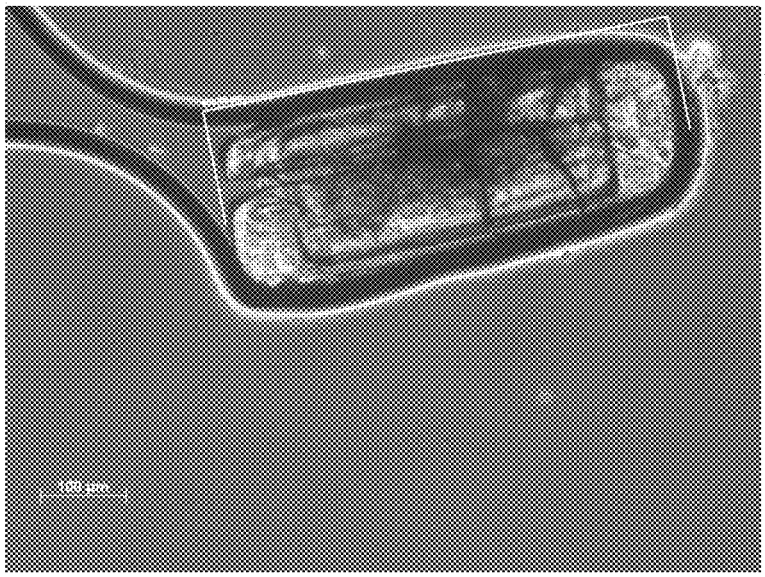
Fig. 7A                        Fig. 7B
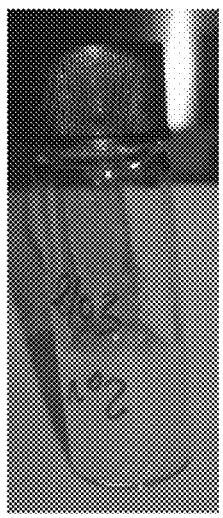 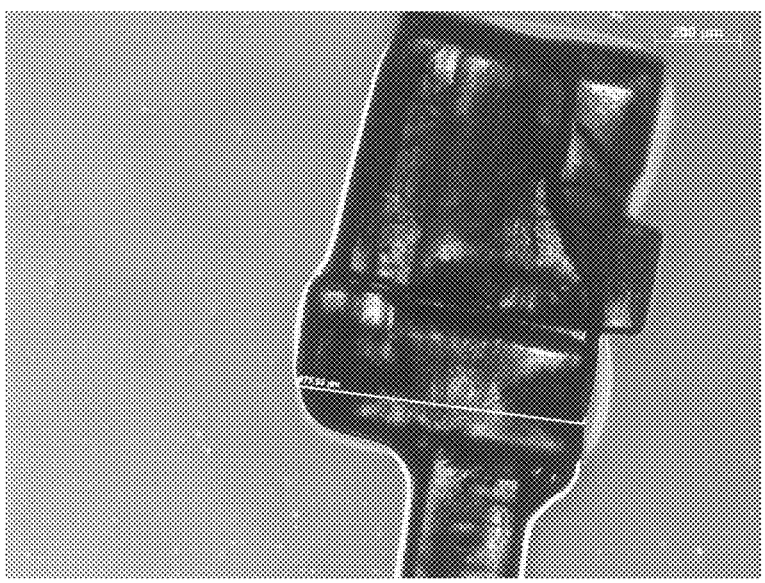
Fig. 8A                        Fig. 8B

ORAL SUSPENSION OF TEMOZOLOMIDE

RELATED APPLICATION(S)

This application claims the benefit of priority of European Patent Application No. 18306683.6 filed on Dec. 13, 2018, the contents of which are incorporated by reference as if fully set forth herein in their entirety.

FIELD AND BACKGROUND OF THE INVENTION

The present invention concerns a pharmaceutical composition comprising temozolomide. Said pharmaceutical composition is a liquid suspension for oral administration or a powder blend for reconstituting said suspension.

Temozolomide is an anticancer drug marketed under trade name Temodal® or Temodar® as well as under generic names. It is used for the treatment of nervous system cancers such as glioblastoma multiform and anaplastic astrocytoma. It is also often used for the treatment of neuroblastoma and Ewing's sarcoma in daily clinical practice.

Two dosage forms of temozolomide are currently commercially available, namely capsules of dosing strength ranging from 5 mg to 250 mg and a powder for injectable solution at 2.5 mg/ml for intravenous injection. The injectable solution is extemporaneously prepared right before the injection by reconstituting the solution with an appropriate solvent, i.e. water for injection.

Currently available solid oral dosage forms, i.e. capsules, are suitable for treatment of adolescent and adult patients able to swallow. However, they are not appropriate for treatment of paediatric patients or for patients unable to swallow suffering from cancers and treated by temozolomide.

Indeed, children of 6 years of age and less are unable to swallow capsules, due to the choking hazard. This is even truer for infants and toddlers. The risk associated with the use of tablets or capsules in young patients is clearly highlighted in the European Medicine Agency Guideline on Pharmaceutical Development of Medicines for Paediatric Use (EMA/CHMP/QWP/180157/2011). Therefore, these patients are usually treated by temozolomide by sprinkling the capsules contents onto soft food like apple sauce or yogurt.

However, this mode of administration is not acceptable considering the following reasons:
  Temozolomide is a water-sensitive drug substance and quickly degrades under humid conditions at neutral or alkaline pH. Therefore, sprinkling the capsules content onto soft food might trigger a significant degradation of temozolomide resulting in an under dosing.
  Temozolomide has a strong bitter and metallic taste which makes its oral administration challenging if not appropriately taste-masked. When the capsule content is mixed with soft food, the taste masking feature provided by the capsule shell no more exists and the taste masking effect of the soft food might not be sufficient. Therefore, administrating temozolomide with soft food might result in an incomplete administration due to spitting and regurgitation caused by the bad taste of temozolomide inappropriately taste-masked.
  Temozolomide is a highly cytotoxic drug and opening capsules would expose parents, care givers and the environment to highly toxic drug particles. To avoid such contamination issues, parents and care givers are encouraged to follow a cumbersome procedure, e.g. preparation with a transparent plastic bag, wearing gloves, goggles and disposable suit.

The aforementioned issues also concern adult patients who are unable to properly swallow capsules such as older patients and those suffering from impairment of deglutition due to their nervous system cancers.

Owing to the increase of temozolomide use in cancer treatments in children, there is an urgent need for the development of new formulations of temozolomide, especially of an age-appropriate formulation. This formulation shall allow a precise control of the dose while ensuring an easy and safe handling by the parents or care givers. This need for an age-appropriate formulation of temozolomide, which allows a dose flexibility for the population of 3 months to 6 years of age and older patients who are not able to swallow, has been highlighted by the European Medicine Agency Draft Inventory of paediatric therapeutic needs (EMA/381728/2014).

There is currently no commercially available drinkable temozolomide formulation. Nevertheless, temozolomide oral suspensions have been developed as unlicensed hospital-compounded preparation by a few research teams.

Trissel et al. (International Journal of Compounding Pharmacy, Vol 10, No. 5, 2006, pp 396-99) have developed a 10 mg/ml oral suspension of temozolomide starting from Temodar® capsules. The detailed composition is provided in Table 1 below. To ensure the homogeneity of the suspension as well as a good acceptability and palatability, ORA-Plus® and ORA-Sweet® (Perrigo) have been used as ready-to-use suspending and flavouring vehicles, respectively. Temozolomide being more stable at low pH, citric acid was incorporated into the formulation. Chemical stability (temozolomide assay >90% of initial content) was demonstrated over 14 days at ambient temperature (23° C.) and 60 days at 4° C. Despite the moderate temozolomide concentration, recrystallisation was observed during the reconstitution of the aqueous suspension, partially resolved by adding povidone K30.

Similarly, Ambados et al. (Journal of Pharmacy Practice and Research, Vol. 42, No. 2, 2012, pp 111-114) have developed a 10 mg/ml oral suspension of temozolomide at pH 4 starting from Temoldal® capsules as well. They also used ORA-Plus® and ORA-Sweet® vehicles as well as citric acid and povidone K30. The detailed composition is provided in Table 1 below. The chemical stability of the suspension was demonstrated over 8 days at ambient temperature (22-23° C.) and 22 days under refrigerated conditions (3-4° C.) respectively.

TABLE 1

Composition of temozolomide hospital-compounded oral suspensions

| | Ambados et al. | | Trissel et al. | |
|---|---|---|---|---|
| | Quantity (mg or ml)/100 ml of suspension | Quantity/ml of suspension | Quantity (mg or ml)/100 ml of suspension | Quantity/ml of suspension |
| Temodal ® 100 mg capsules | 10 (eq. 1000 mg TMZ) | eq. 10 mg/ml | 10 (eq. 1000 mg TMZ) | eq. 10 mg/ml |
| Povidone K30 | 500 | 5 mg/ml | 500 | 5 mg/ml |
| Citric acid (monohydrate) | 27.3 | 0.273 mg/ml | — | — |
| Citric acid (anhydrous) | — | — | 25 | 0.25 mg/ml |
| Purified water | 1.5 ml | 0.015 ml | 1.5 ml | 0.015 ml |
| Ora-Plus ® | 45 ml | 0.45 | 50 ml | 0.50 |
| Ora-Sweet ® | qs 100 ml | qs 1 ml | qs 100 ml | qs 1 ml |

The suspensions prepared by Trissel et al. and Ambados et al. are then essentially similar in composition and can be used as a suitable alternative for the paediatric patients. However, it is practically impossible to increase the drug load above 10 mg/ml since these preparations are prepared from Temodar® capsules which contain a significant amount of excipients impacting the viscosity of the oral suspension. Hence, increasing the temozolomide concentration in the suspension would result in increasing the viscosity of the suspension which would eventually hamper the oral administration using oral syringes. In addition, it is preferred to keep the administration volume as low as possible in children, typically less than 5 ml to avoid risks of regurgitation. As temozolomide dose can go up to ca. 150 mg per administration in children, this would result in administering 10 to 15 ml of the 10 mg/ml oral suspension which is not an ideal administration volume. The maximum recommended single dosing volume is 5 ml for children aged below 4 years and 10 ml for children aged between 4 and 12 years according to EMA draft guidance (EMA/CHMP/QWP/180157/2011).

Furthermore, it appears that there is a change in the solid form of the drug substance, which recrystallises during the reconstitution of the oral suspension. Such recrystallisation may impair the quality of the medicine, especially with regard to the accuracy of the dose dispensed, the kinetic of solubilisation, or the clogging of syringe for oral administration, if the crystals formed are too large. This suggests that the performance of hospital-compounded suspensions, with respect to dose uniformity, dissolution kinetic, may significantly vary from a batch to another. This could result in administering an inappropriate dose to patients.

There is currently no commercially available product addressing the aforementioned issues. Especially, there is no drinkable temozolomide formulation commercially available for the paediatric population and patients with swallowing difficulties.

SUMMARY OF THE INVENTION

Pursuing its efforts in development of useful paediatric formulation in oncology, the Applicants have developed a particular pharmaceutical composition of temozolomide. The composition of the invention is an oral suspension which is stable in aqueous medium. It can be available as a ready-to-use oral suspension or can be easily prepared extemporaneously from a powder blend by addition of water or another appropriate liquid vehicle. Moreover, in addition to further advantages which will be detailed below, it is possible for the first time to get a composition with a drug load higher than 10 mg/ml, advantageously higher than 20 mg/ml or even equal to or higher than 40 mg/ml.

DESCRIPTION OF SPECIFIC EMBODIMENTS OF THE INVENTION

According to a first aspect, the present invention concerns a pharmaceutical composition comprising:
  temozolomide or a salt thereof;
  at least one agent controlling the solid state of temozolomide in suspension;
  a pharmaceutically acceptable liquid vehicle, advantageously water;
  optionally at least one acid in a quantity so that the pH of the composition is below 5.

According to one embodiment, the pharmaceutical composition according to the invention is a liquid suspension. In case of the pharmaceutically acceptable liquid vehicle being water, the composition is an aqueous suspension. According to another embodiment, the pharmaceutical composition of the invention is a ready-to-use suspension.

According to an usual definition, a suspension is a liquid in which solid particles (i.e. temozolomide particles) are dispersed in a liquid phase but not fully dissolved.

In the frame of the invention, "a pharmaceutically acceptable liquid vehicle" means a liquid carrier which allows preparation of a suspension and with which the therapeutic agent (i.e temozolomide) is administered. In a specific embodiment, the term "pharmaceutically acceptable" means approved by a regulatory agency of the Federal or a state government or listed in the U.S. Pharmacopeia or European Pharmacopeia or other generally recognized pharmacopeia for use in animals, and humans. Suitable pharmaceutical vehicles includes: water, ethanol, polyethylene glycol (PEG), glycerol, propylene glycol and mixtures thereof.

According to another specific embodiment, the pharmaceutical composition according to the invention can be in a solid form, advantageously a powder blend or mixture. The composition of the present invention is advantageously a powder for reconstitution of suspension which extemporaneously forms the suspension upon addition of the pharmaceutically acceptable liquid vehicle. In one embodiment of the invention, the reconstitution vehicle is water.

Therefore and according to another aspect, the present invention also concerns a powder blend comprising temozolomide or a salt thereof and at least one agent controlling the solid state of temozolomide in suspension.

According to a specific embodiment, the powder blend further contains at least one acid in an adequate quantity so that after suspending the powder blend in the liquid vehicle, advantageously water, the suspension so obtained has a pH below 5.

As reported below, it has been observed that the blend of powders for reconstitution of the suspension immediately forms a homogeneous suspension upon addition of the vehicle.

Moreover, the composition of the invention allows a precise dosing and an easy adaptation of the dose by varying the volume of administration in a unit dose whereas multiple capsules are usually required to adjust the dose to the patient's body surface area.

As already disclosed, a pharmaceutical composition according to the invention contains, as an active ingredient, temozolomide or a pharmaceutically acceptable salt thereof.

Temozolomide (or TMZ) is an active pharmaceutical ingredient used in oncology and acting as a DNA alkylating agent. Temozolomide is known as 3-methyl-4-oxoimidazo[5,1-d][1,2,3,5]tetrazine-8-carboxamide and presents the following chemical structure.

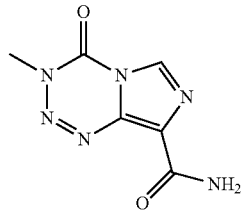

Temozolomide can also be used as pharmaceutically acceptable salts.

Temozolomide can be procured from various sources:
from commercially available capsules, each containing 5 mg to 250 mg of temozolomide, e.g. commercialized under the brand name Temodal®;
as raw material supplied by manufacturers of active pharmaceutical ingredients.

In one embodiment of the invention, the concentration of temozolomide in the suspension widely varies, e.g. ranges from 5 to 100 mg/ml. Moreover and according to the invention, the claimed specific formulation allows to reach high concentrations in temozolomide never reached in the prior art to the knowledge of the Applicants. Advantageously, the temozolomide concentration in the suspension is higher than 10 mg/ml (1% w/v), more advantageously equal to or higher than 15 mg/ml, 20 mg/ml, 25 mg/ml, 30 mg/ml, 35 mg/ml or even 40 mg/ml. According to specific embodiments, the concentration ranges from 20 to 60 mg/ml, from 20 to 50 mg/ml or from 30 to 50 mg/ml. The concentrations between 20 mg/ml (2% w/v) and 40 mg/ml (4% w/v) are particularly preferred, since they allow to administer the medicine in a reasonable volume of liquid to infants and children and to limit regurgitation. Temozolomide may represent between 0.5 and 10% (w/v) of the composition, advantageously between 1 and 5% (w/v).

Characteristically, the composition of temozolomide according to the invention further contains at least one agent controlling the solid state of temozolomide in suspension. Indeed and during the development of the compositions of the invention, the Applicants observed an erratic recrystallisation of temozolomide after reconstitution of some suspensions with water. The recrystallisation process formed macroscopic crystals larger than 500 µm whereas the temozolomide drug substance entering the composition had a particle size in the lower micrometric range (d90<100 µm). The recrystallisation triggered dose inhomogeneity within the suspensions, with large crystals settling down the bottom of the bottle or container. Furthermore, large crystals tended to clog the syringe for oral administration. This recrystallisation phenomenon was also observed in compositions containing povidone, the excipient used in the hospital-compounded formulations developed by Trissel et al. and Ambados et al.

According to one embodiment, the agent controlling the recrystallisation of temozolomide, and thus the solid state thereof in suspension, is an inorganic agent, advantageously water-insoluble. According to a specific embodiment, said agent contains silicon (Si), i.e. is a silicon derivative possibly in the form of silica or silicate, advantageously silica (silicon dioxide). Preferably, said agent is selected from the group consisting of: colloidal silica, hydrophobic colloidal silica, fumed silica, mesoporous silica, bentonite, saponite, kaolin, magnesium aluminium silicate, more preferably mesoporous silica, their derivatives and their mixtures.

As known in the art, mesoporous silica is a mesoporous form of silica, i.e. advantageously with pore diameters between 2 and 50 nm. It has a highly developed network of mesopores that provide access to a large surface area.

Mesoporous silica can be further defined by:
a bulk density less than to 1 g/ml, advantageously less than or equal to 0.5 g/ml, 0.4 g/ml, 0.3 g/ml, 0.2 g/ml, or even less than or equal to 0.1 g/ml; and/or
a specific surface area (as measured e.g. by the BET method) greater than 200 m$^2$/g, advantageously greater than or equal to 250 m$^2$/g, 300 m$^2$/g, 350 m$^2$/g, 400 m$^2$/g, 450 m$^2$/g, 500 m$^2$/g, 1000 m$^2$/g, 1500 m$^2$/g, 2000 m$^2$/g, 2500 m$^2$/g or even greater than or equal to 3000 m$^2$/g.

Examples of commercially available mesoporous silica are those sold by GRACE under the name SYLOID®, especially FP (e.g. AL-1 or 244) or XDP (e.g. 3050). Alternatively, they can be of MAM-41 or SBA-15 type.

According to a specific embodiment, such an agent, especially silica, its derivatives or their mixture, represent between 0.05 and 10% (w/v) of the composition according to the invention, advantageously between 0.1 and 1%, e. g. 0.1 or 0.2%.

As shown in the examples below, the presence of such an agent in the composition of the invention (i.e. in the liquid composition or in the powder blend) allows to obtain a suspension with at least one of the following features, preferably all the following features:

A suspension which contains temozolomide in the form of temozolomide monohydrate: a rapid in-situ conversion of anhydrous form of temozolomide into temozolomide monohydrate occurs upon reconstitution of the suspension with water or the aqueous vehicle or during preparation of the aqueous suspension.

A suspension which contains temozolomide monohydrate exhibiting a particle size distribution of temozolomide particles which is compatible with the use as an oral suspension, i.e. which does not settle too rapidly in the suspension, or does not clog the syringe for oral administration and maintains the suspension homogeneity.

Along with the investigation of the temozolomide crystal formation within the suspension (see example 3-1 below), the Applicants noticed that the solid-state properties of temozolomide changed in aqueous suspension. The solid-state properties of the temozolomide drug substance entering the composition of the powder for reconstitution corresponded to the polymorph Form III as disclosed in US 2005/0187206 (Form III also named Form 1 in Cambridge Structural Database (CCDC): ref 665060, anhydrous form), whereas the solid-state form of temozolomide in suspension was found to match with the temozolomide monohydrate (CCDC ref 665056).

It is to be noted that temozolomide monohydrate is not a new solid-state form of temozolomide per se and its preparation has already been disclosed in e.g. document WO 2008/111092, using a synthetic process which consisted of recrystallising temozolomide from a mixture of water and water-miscible solvents. However, to the Applicants' knowledge, it is the first time that spontaneous in-situ formation of temozolomide monohydrate is reported.

- A rapid transition from anhydrous temozolomide (form III) to temozolomide monohydrate: advantageously in less than 24 h, preferably in less than 12 h, more preferably in less than 6 hours, more preferably in less than 1 hour, even more preferably in less than 10 minutes after the suspension reconstitution (i.e. the addition of the liquid vehicle, advantageously water).

As mentioned above, a physical solid-state change occurred in all the aqueous suspension prepared from temozolomide Form III (i.e. anhydrous temozolomide) and a single new solid-state form was produced: temozolomide monohydrate. However, it was shown that the conversion from temozolomide form III into temozolomide monohydrate after reconstitution of the suspension significantly varies depending on the composition of the suspensions (see example 3-2). Surprisingly, the Applicants discovered that the conversion of temozolomide Form III into temozolomide monohydrate is almost instantaneous in the compositions of the invention containing silica derivatives whereas it may take several hours in other compositions. A fast recrystallisation is usually required to form small crystals whereas a longer crystallisation tends to form larger crystals.

- A controlled and homogeneous size of the temozolomide monohydrate particles, with a d90 value advantageously equal to or less than 500 μm, more advantageously equal or less than 250 μm, preferably equal or less than 100 μm. As known by the skilled person, it means that 90% of a sample's mass (number-based distribution) has a particle diameter inferior to this value.

As shown below (see example 4), the compositions of the invention exhibit a good physical homogeneity and stability, with particle temozolomide monohydrate particle size below 100 μm (d90 value), remaining homogeneous and showing no irreversible precipitation or sedimentation for 60 days under refrigerated conditions and several days at ambient temperature.

It is to be noted that controlling the particle size in the oral suspension of temozolomide is a critical quality attribute to allow a homogeneous suspension and an accuracy of the dose dispensed.

Unexpectedly, the Applicants identified that the addition of specific agents as disclosed above allows controlling the kinetic of the conversion of temozolomide into temozolomide monohydrate and the size of the crystals so obtained in suspension.

According to a preferred embodiment and in the frame of the invention, an agent controlling the solid state of temozolomide in suspension is defined as an agent, advantageously an inorganic water-insoluble ingredient, more advantageously a silicon-, silicon oxide, silica- or silicate-based compound, which has the following properties when added in a suspension containing temozolomide or in a powder blend dedicated to the reconstitution of such a suspension:

(i) controls the kinetic of recrystallisation of temozolomide, i.e. allows the conversion of the anhydrous form of temozolomide into temozolomide monohydrate in less than 24 h, preferably in less than 12 h, more preferably in less than 6 hours, more preferably in less than 1 hour, even more preferably in less than 10 minutes after the suspension reconstitution (i.e. the addition of the liquid vehicle, advantageously water); and/or (ii) controls the crystal size of temozolomide monohydrate particles in suspension, i.e. allows obtaining of particles with a d90 value equal to or less than 500 μm or even 100 μm, advantageously even after 60 days under refrigerated conditions (2-8° C.) and several days at ambient temperature (20-25° C.).

This is the first time, to the Applicants' knowledge, that silicon derivatives such as silica are reported to affect the recrystallisation of an organic substance in suspension. Indeed, silica has been reported in pharmaceutical compositions as an excipient acting as a glidant or a lubricant, but never to control the solid state of an organic substance in suspension, or a recrystallisation process.

According to a further embodiment, a composition according to the invention, advantageously a suspension, more advantageously an aqueous suspension, exhibits an acidic pH, advantageously lower than 5, more advantageously lower than or equal to 4.5, more advantageously lower than or equal to 4. A preferred range of pH is from 3.8 to 2.8, or even from 3.6 to 3.

In one embodiment and especially when water is used as a liquid vehicle, such a pH range can be obtained by the addition of an adequate quantity of an acid in the suspension or in the powder blend. Therefore, and in one embodiment of the invention, the composition contains one or more pharmaceutically acceptable acids. They are preferentially selected among the organic and inorganic acids. Advantageously, the organic acids are selected among: citric acid, malic acid, tartaric acid, fumaric acid, lactic acid, pentetic acid, succinic acid and maleic acid. Advantageously, the inorganic acid is selected among: phosphoric acid, hydrochloric acid and sulfuric acid. Salts and mixtures thereof are also contemplated in the frame of the invention.

According to a specific embodiment, a composition according to the invention contains citric acid and/or tartaric acid.

On one aspect, the acid(s) represents between 0 and 10% (w/v) of the composition according to the invention so that the pH of the suspension is not more than 5.0.

In another embodiment of the invention, the composition comprises at least a further ingredient or excipient. Of particular interest for preparing a suspension are the so-called suspending agents. Suspending agent, thickening agent and viscosity-increasing agent can be used indifferently with respect to this invention. Many pharmaceutically acceptable suspending agents are available, usually in a powder form.

A non-limiting list of further excipients to be used alone or in combination in a composition according to the invention is provided hereunder:

Cellulose or a derivative thereof: microcrystalline cellulose, methylcellulose, ethylcellulose, hydroxymethylcellulose, hydroxyethylcellulose, hydroxypropylcellulose, hydroxypropylmethylcellulose, hydroxyethylmethylcellulose, carboxymethylcellulose and salt thereof (e.g. carboxymethylcellulose sodium or carboxymethylcellulose calcium), or a mixture thereof as e.g. co-processed microcrystalline cellulose and carboxymethyl cellulose sodium;

Starch or a derivative thereof or a mixture thereof: corn starch, potato starch, rice starch, wheat starch, tapioca starch, sodium starch glycolate (SSG), pregelatinized starch, hydroxypropylstarch, coprocessed corn starch and lactose monohydrate;

polysaccharide-based natural gums such as xanthan gum, tragacanth or guar gum;

Polyvinylpyrrolidone (PVP or povidone), advantageously povidone K30;

Poloxamers;

Carbomers

Cyclodextrins, e.g. α-cyclodextrin, β-cyclodextrin, γ-cyclodextrin, hydroxypropyl-β-cyclodextrin, sulfonylbutlyether-β-cyclodextrin;

Gelatine;

Carraghenans;

Alginic acid or salt thereof: sodium alginate, calcium alginate, ammonium alginate, potassium alginate;

Chitosan;

Copolymer of ethylene oxide and propylene oxide;

Acrylic acid-based polymers;

Polycarbophil;

Polydextrose;

Polyethylene glycol;

Hyaluronic acid or salt thereof, such as sodium hyaluronate or calcium hyaluronate.

According to one embodiment, said further ingredient(s) represents between 0.1 and 20% (w/v) of the composition according to the invention.

In another aspect of the invention, the composition may contain sweeteners and/or flavouring agents to provide the composition with taste-masking properties and make the administration to children easier. Advantageously, the flavouring agents are selected from the following list of flavour but not limited thereto: cherry, orange, citrus, lime, mint, strawberry, raspberry, cola, banana, vanilla, peppermint, caramel. Advantageously, the flavouring agent is cola, lime or mint. More advantageously, the flavouring agent is cola. Advantageously, the sweetener is selected from the following list of pharmaceutically acceptable sweeteners but not limited to: sucrose, sucralose, saccharin, sodium saccharin, acesulfam K, xylitol.

According to one embodiment, said sweeteners and/or flavouring agents represent between 0.05 and 5% (w/v) of the composition according to the invention.

In one embodiment, the composition may contain additional pharmaceutically acceptable ingredients providing the composition with better stability features. The composition may notably contain preservatives. Advantageously, the composition does not contain parabens (alkyl parahydroxybenzoate) as preservatives.

A non-limiting list of compositions of suspensions according to the invention is provided hereunder:

| A/ | |
|---|---|
| Ingredients | Quantity % w/v |
| Temozolomide | 1 to 5% |
| Xanthan gum | 0.1 to 2% |
| Povidone | 0.1 to 5% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

| B/ | |
|---|---|
| Ingredients | Quantity % w/v |
| Temozolomide | 1 to 5% |
| Xanthan gum | 0.1 to 2% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

| C/ | |
|---|---|
| Ingredients | Quantity % w/v |
| Temozolomide | 1 to 5% |
| Xanthan gum | 0.1 to 2% |
| Colloidal silica | 0.1 to 10% |
| Tartaric acid | 0.1 to 2% |
| Citric acid | 0 to 2% |
| Sweetener (Sucralose, Saccharin, acesulfam K . . . ) | 0.05 to 1% |
| Flavour | 0.05 to 1% |
| Water | qs |

| D/ | |
|---|---|
| Ingredients | Quantity % w/v |
| Temozolomide | 1 to 5% |
| Sodium starch glycolate | 0.1 to 10% |
| Povidone | 0 to 10% |
| Mesoporous silica | 0.1 to 10% |
| Tartaric acid | 0.1 to 2% |
| Citric acid | 0 to 2% |
| Sweetener (Sucralose, Saccharin, acesulfam K . . . ) | 0.05 to 1% |
| Flavour | 0.05 to 1% |
| Water | qs |

| E/ | |
|---|---|
| Ingredients | Quantity % w/v |
| Temozolomide | 1 to 5% |
| Xanthan gum | 0.1 to 2% |
| Sodium starch glycolate | 0.1 to 10% |
| Povidone | 0 to 10% |
| Mesoporous silica | 0.1 to 10% |
| Tartaric acid | 0.1 to 2% |
| Citric acid | 0 to 2% |
| Sweetener (Sucralose, Saccharin, | 0.05 to 1% |

E/

| Ingredients | Quantity % w/v |
| --- | --- |
| acesulfam K . . . ) | |
| Flavour | 0.05 to 1% |
| Water | qs |

F/

| Ingredients | Quantity % w/v |
| --- | --- |
| Temozolomide | 1 to 5% |
| Xanthan gum | 0.1 to 2% |
| Carboxymethylcellulose Sodium | 0.1 to 10% |
| Povidone | 0 to 10% |
| Mesoporous silica | 0.1 to 10% |
| Tartaric acid | 0.1 to 2% |
| Citric acid | 0 to 2% |
| Sweetener (Sucralose, Saccharin, acesulfam K . . . ) | 0.05 to 1% |
| Flavour | 0.05 to 1% |
| Water | qs |

G/

| Ingredients | Quantity % w/v |
| --- | --- |
| Temozolomide | 1 to 5% |
| Carboxymethylcellulose Sodium | 0.1 to 10% |
| Povidone | 0 to 10% |
| Mesoporous silica | 0.1 to 10% |
| Citric acid | 0 to 2% |
| Sweetener (Sucralose, Saccharin, acesulfam K . . . ) | 0.05 to 1% |
| Flavour | 0.05 to 1% |
| Water | qs |

H/

| Ingredients | Quantity % w/v |
| --- | --- |
| Temozolomide | 1 to 5% |
| Carboxymethylcellulose Sodium | 0.1 to 10% |
| Mesoporous silica | 0.1 to 10% |
| Tartaric acid | 0.1 to 2% |
| Citric acid | 0 to 2% |
| Sweetener (Sucralose, Saccharin, acesulfam K . . . ) | 0.05 to 1% |
| Flavour | 0.05 to 1% |
| Water | qs |

I/

| Ingredients | Quantity % w/v |
| --- | --- |
| Temozolomide | 1 to 5% |
| Carboxymethylcellulose Sodium | 0.1 to 10% |
| Colloidal silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

J/

| Ingredients | Quantity % w/v |
| --- | --- |
| Temozolomide | 1 to 5% |
| Methylcellulose | 0.1 to 10% |
| Povidone | 0 to 10% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

K/

| Ingredients | Quantity % w/v |
| --- | --- |
| Temozolomide | 1 to 5% |
| Hydroxypropylmethylcellulose | 0.1 to 10% |
| Povidone | 0 to 10% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

L/

| Ingredients | Quantity % w/v |
| --- | --- |
| Temozolomide | 1 to 5% |
| Hydroxyethylmethylcellulose | 0.1 to 10% |
| Povidone | 0 to 10% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

M/

| Ingredients | Quantity % w/v |
| --- | --- |
| Temozolomide | 1 to 5% |
| Hydroxypropylcellulose | 0.1 to 10% |
| Povidone | 0 to 10% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

N/

| Ingredients | Quantity % w/v |
| --- | --- |
| Temozolomide | 1 to 5% |
| Ethylcellulose | 0.1 to 10% |
| Povidone | 0 to 10% |
| Mesoporous silica | 0.1 to 10% |

N/

| Ingredients | Quantity % w/v |
| --- | --- |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

O/

| Ingredients | Quantity % w/v |
| --- | --- |
| Temozolomide | 1 to 5% |
| Cellulose microcrystalline/carboxymethylcellulose sodium | 1 to 5% |
| Povidone | 0 to 5% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

P/

| Ingredients | Quantity % w/v |
| --- | --- |
| Temozolomide | 1 to 5% |
| Carbomer | 0.1 to 5% |
| Povidone | 0 to 5% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

Q/

| Ingredients | Quantity % w/v |
| --- | --- |
| Temozolomide | 1 to 5% |
| Tragacanth | 0.1 to 5% |
| Mesoporous silica | 0.1 to 10% |
| Povidone | 0 to 5% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

R/

| Ingredients | Quantity % w/v |
| --- | --- |
| Temozolomide | 1 to 5% |
| Guar gum | 0.1 to 5% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.05 to 1% |
| Flavour | 0.05 to 1% |
| Water | qs |

S/

| Ingredients | Quantity % w/v |
| --- | --- |
| Temozolomide | 1 to 5% |
| Poloxamer | 1 to 20% |
| Mesoporous silica | 0.1 to 10% |
| Tartaric acid | 0 to 2% |
| Citric acid | 0.1 to 2% |
| Sweetener (Sucralose, Saccharin, acesulfam K . . . ) | 0.1 to 1% |
| Flavour | 0.1 to 1% |
| Water | qs |

Noticeably, the composition of the invention exhibits a good chemical stability in temozolomide, i.e. a temozolomide assay equal to or higher than 90% of the initial content. According to a specific embodiment, such a good chemical stability is observed for more than 60 days or even for up to 5 months under refrigerated conditions (2-8° C.) (see example 2 for the protocol and results). In other words and advantageously, temozolomide exhibits an assay higher that 90% of the initial assay value for at least 15 days, preferably at least 30 days, more preferably at least 60 days, more preferably at least 5 months, even more preferably 12 months if the composition of the invention is stored under refrigerated conditions (2-8° C.).

In addition and surprisingly, the composition of the invention can be stored more than 30 days at room temperature (20-25° C.) protected from light without significant degradation. This high chemical stability was unexpected considering published stability of hospital-compounded suspensions developed by Ambados et al. and Trissel et al. In other words, the composition exhibits a good chemical stability in suspension or after reconstitution with water, meaning that at least 90% of the initial content of temozolomide is recovered after at least 30 days of storage at ambient condition (20-25° C.).

In one further embodiment of the invention, the composition is a suspension which can be easily given orally to any kind of patient population and especially to children and adults suffering from dysphagia or having difficulties to swallow monolithic dosage forms such as tablets and capsules. Advantageously the composition of the invention allows administration of small volumes which limits the risk of regurgitation and resulting in under dosing.

In one further embodiment of the invention, the composition is compatible with an oral or gastric administration using an appropriate medical device, e.g. a syringe for oral use and/or a gastric tube.

In one embodiment of the invention, the composition is administered by oral route (per os) as a drinkable dosage form. In another embodiment, the composition is administered by gastric route. Advantageously the composition of the invention is compatible with polymers used in the manufacture of oral administration devices such as syringes for oral use or feeding tubes. Advantageously, the composition of the invention is stable in contact with polypropylene and polyethylene. Of particular interest, the administration of the composition using a syringe for oral use allows a precise dosing and mitigates the risks of inappropriate dosing regimen.

In one embodiment of the invention, the composition is stored in syringes for oral use after reconstitution with water. Advantageously, the syringe for oral use according to the invention is made of polypropylene and/or polyethylene.

Noticeably, the syringes for oral use allow the administration of a predefined dose of temozolomide to patient on a daily basis while limiting the risks of accidental exposure to patients or caregivers.

In one embodiment of the invention, each syringe contains a dose of temozolomide ranging from 10 to 250 mg.

Advantageously, the composition of the invention shows a good stability in syringe after reconstitution with water for at least 15 days under refrigerated conditions (2-8° C.).

The present invention also concerns the use of the compositions as disclosed in medicine, advantageously in oncology, more advantageously for treating nervous system cancers.

According to specific embodiments, the compositions of the invention are used for treating glioma, advantageously glioblastoma multiform, anaplastic astrocytoma, neuroblastoma or Ewing's sarcoma.

According to one embodiment, the liquid suspension is produced using state-of-the-art manufacturing processes of suspension and equipment, e.g. using pharmaceutical reactor equipped with various stirring and/or homogenizing modules. For instance, excipients and temozolomide are dispersed in the suspension vehicle and mixed together in the pharmaceutical reactor until a homogeneous suspension is reached.

Therefore and according to another aspect, the invention relates to a method for preparing a pharmaceutical composition, advantageously a suspension, comprising mixing in a reactor or a vessel:
  temozolomide or a salt thereof;
  at least one agent controlling the solid state of temozolomide in suspension as defined above;
  a pharmaceutically acceptable liquid vehicle, advantageously water; and optionally before, simultaneously or after, adding an adequate quantity of acid so that the pH of the composition is below 5.

According to another embodiment, the powder blend for reconstitution is produced using state-of-the-art manufacturing processes of powder blend and equipment, e.g. powder blending in blender, dry granulation using roller compactor, wet granulation using high shear granulator or fluid bed granulator for instance.

In relation to this embodiment, the invention relates to a method for preparing a liquid suspension, advantageously an aqueous suspension as disclosed above, comprising:
  suspending the powder blend in an adequate volume of the liquid vehicle, advantageously water; and optionally
  before, simultaneously or after, adding an adequate quantity of acid so that the pH of the composition is below 5.

The invention will be further illustrated by the following figures and examples. However, these examples and figures should not be interpreted in any way as limiting the scope of the present invention.

BRIEF DESCRIPTION OF THE SEVERAL VIEWS OF THE DRAWINGS

FIG. 7: Macroscopic (A) and microscopic (B) evaluation of composition #11

FIG. 8: Macroscopic (A) and microscopic (B) evaluation of composition #12

EXAMPLES

Figure 1:
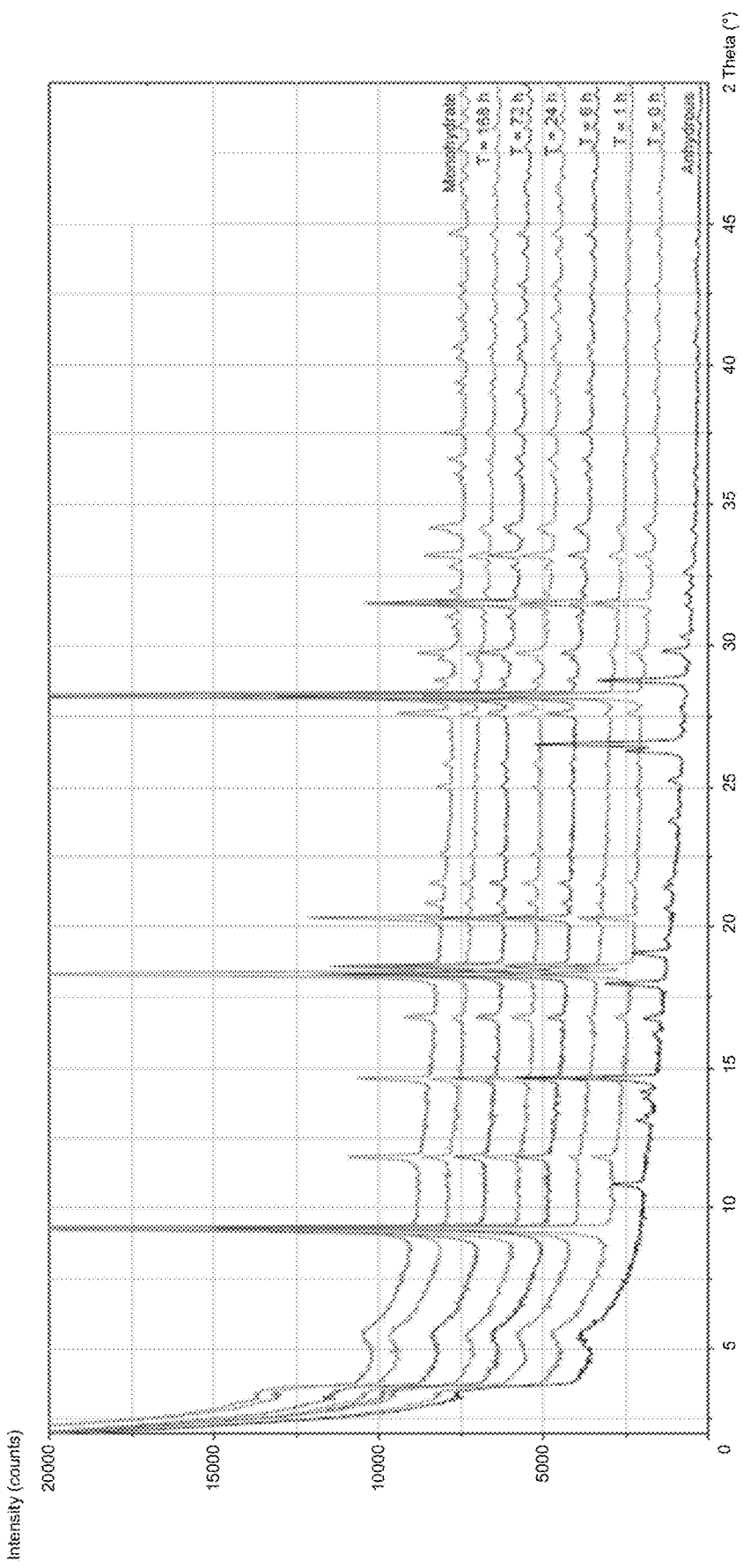
FIG. 1: XRPD diffractograms of composition #8, of anhydrous TMZ (Form III) and of TMZ monohydrate

1/Preparation of the Compositions 1-1 Powder Blends:

The compositions were prepared according to the protocol detailed hereunder:
  1. Excipients were individually weighed and blended until a homogeneous powder was obtained. Temozolomide was weighed and added to the blend of excipients.
  2. The powder blend was gently mixed until a homogeneous powder blend was obtained.
  3. The homogeneous powder blend was then poured into amber vials made of glass or PET.
  4. An appropriate volume of water was then added onto the powder blend to obtain a 40 mg/ml temozolomide suspension.
  5. Right after addition of water, the bottle was closed and vigorously shaken for at least 30 seconds, either by hand or using shaking devices.
  6. Suspensions were then stored in amber glass or PET bottle under refrigerated conditions and analysed for the following parameters:
    Appearance
    Temozolomide assay
    pH
    Physical characteristics (polymorphism, particle size)

A list of the compositions so prepared is presented in table 2 hereunder. Mesoporous silica has been used as an example of an agent controlling the solid state of temozolomide (TMZ) in suspension.

TABLE 2

Composition of various temozolomide formulations (concentrations expressed in mg/ml)

| Composition # | 1 | 2 | 3 | 4 | 5 | 6 | 7 | 8 | 9 | 10 | 11 | 12 |
|---|---|---|---|---|---|---|---|---|---|---|---|---|
| TMZ Supplier 1 | 40 | | 40 | 40 | | | 40 | 40 | 40 | | 40 | 40 |
| TMZ Supplier 2 | | 40 | | | | | | | | | | |
| TMZ Supplier 3 | | | | | 40 | 40 | | | | 40 | | |
| Xanthan gum (XG) | 7.5 | 7.5 | 2.4 | 2.4 | 5 | 5 | 5 | 5 | 2.5 | 2.5 | 5 | 2.5 |
| Sodium starch Glycolate (SSG) | | | 65 | 65 | | | | | 25 | 25 | | 25 |
| PVP K30 | 40 | 40 | 20 | 20 | 40 | 40 | 20 | 20 | 20 | 40 | 20 | 20 |
| Mesoporous silica | | | 10 | | 20 | 10 | 10 | 10 | 10 | 10 | | |
| Poloxamer 407 | | | | 10 | | | | | | | | |
| Citric acid | 9 | 6 | 7 | 7 | 7 | 7 | 7 | 5 | 7 | 7 | 5 | 7 |
| Sucralose | 3 | | 3 | 3 | 3 | 3 | 3 | 3 | 3 | 3 | 3 | 3 |
| Cola flavour | 5 | 5 | 5 | 5 | 5 | 5 | 5 | 5 | 5 | 5 | 5 | 5 |
| Appearance | NC | NC | C | NC | C | C | C | C | C | C | NC | NC |
| Assay* | | | T0 = 102% T12d = 103% | T0 = 99.5% T7d = 45.8% | T0 = 98.5% T7d = 97% | T0 = 99.2% T7d = 96.5% | T0 = 98.6% T7d = 103% T28d = 100.5% | T0 = 99.2% T15d = 97.8% | T0 = 102.4% T15d = 101.2% | T0 = 102.1 T73d = 92.4 | T1d = 24% | T1d = 52% |
| pH | 2.8 | N/A | 4 | 4 | 2.9 | 2.9 | 2.8 | 2.9 | 3.5 | 3.6 | 2.9 | 3.5 |

C: Complies, i.e. homogeneous suspension and temozolomide dosage assay within 90-110% of title
NC: Non-compliant, i.e. non-homogeneous suspension with recrystallisation of temozolomide into macroscopic crystals; temozolomide dosage assay non-compliant
*Low assay values are related to crystallisation of temozolomide forming large crystals leading to an inhomogeneous suspension and not to a chemical degradation of temozolomide Table 2 reveals that only compositions containing mesoporous silica (i.e. #3 and #5 to #10) are compliant, with a proper physical appearance and a suitable temozolomide concentration. More specifically:

Composition #11 can be compared with composition #8;
Composition #12 can be compared with composition #9.

1-2 Ready-to-Use Suspensions:

Ready-to-use suspensions were prepared according to the process detailed hereunder.
1. Excipients were individually weighed and blended until a homogeneous powder was obtained.
2. Excipients were added into the suspension vehicle (i.e. water) contained into a stirring vessel
3. Temozolomide was weighed and added to the aqueous dispersion of excipients.
4. The temozolomide suspension was stirred for ca. 30 min until the suspension was visually homogeneous.
5. The homogeneous suspension was then poured into amber vials made of glass.

TABLE 3

Composition of various temozolomide (TMZ) suspensions (concentrations expressed in mg/ml)

| Composition # | 13 | 14 | 15 | 16 | 17 |
|---|---|---|---|---|---|
| TMZ Supplier 1 | — | 40 | — | — | — |
| TMZ Supplier 2 | — | — | 40 | — | — |
| TMZ Supplier 3 | 40 | — | — | 40 | 40 |
| Xanthan gum (XG) | 5 | 5 | 5 | 5 | 5 |
| PVP K30 | 20 | — | — | — | — |
| Mesoporous silica | 10 | 1 | 1 | — | — |
| Colloidal silica | — | — | — | 1 | — |
| Anhydrous colloidal silica | — | — | — | — | 1 |
| Citric acid | 5 | 5 | 5 | 5 | 5 |
| Sucralose | 3 | 3 | 3 | 3 | 3 |
| Cola flavour | 5 | 5 | 5 | 5 | 5 |
| Water | qs | qs | qs | qs | qs |
| Appearance of the suspension 96 h after preparation | C | C | C | C | C |
| Assay* | T0 = 99.6% | T0 = 98.8% T21 d = 99.1% | T0 = 97.5% T21 d = 98.1% | NP | NP |
| pH | 3.0 | 3.0 | 3.0 | NP | NP |

NP: not performed

These examples reveal that the properties of composition #13 (identical to composition #8 except for the TMZ supplier) are conserved even:

in the absence of PVP K30;

if the quantity of mesoporous silica is decreased;

if mesoporous silica is replaced by another source of silicon dioxide, e.g. colloidal silica or anhydrous colloidal silica.

2/Stability of Reconstituted Suspensions

The chemical stability of some samples of compliant formulations was studied over several weeks at 4° C. and room temperature (20-25° C.). The suspensions were analysed for the temozolomide content by HPLC and the remaining content vs the theoretical content was calculated. Stability results of compositions #8 (Table 4), #9 (Table 5), #5 (Table 6) and #6 (Table 7) in % are provided hereunder.

TABLE 4

Stability of composition #8

| T °C. | Day 1 | Day 7 | Day 14 | Day 26 | Day 36 | Day 60 |
|---|---|---|---|---|---|---|
| 4° C. | 99.5 | — | — | — | 95.2 | — |
| 20-25° C. | 99.2 | 98.3 | 99.1 | 98.5 | 94.4 | 89.5 |

TABLE 5

Stability of composition #9

| T °C. | Day 1 | Day 7 | Day 14 | Day 26 | Day 36 | Day 60 |
|---|---|---|---|---|---|---|
| 4° C. | 102.9 | — | — | — | 98.7 | — |
| 20-25° C. | 102.0 | 101.1 | 101.2 | 97.5 | 98.0 | 91.1 |

Furthermore, some formulation prototypes were analysed several months after preparation and storage at 4° C.

TABLE 6

Stability of composition #5

| T° C. | Day 1 | 5 Months |
|---|---|---|
| 4° C. | 98.5 | 102.0 |

TABLE 7

Stability of composition #6

| T° C. | Day 1 | 5 Months |
|---|---|---|
| 4° C. | 99.2 | 102.4 |

Surprisingly, the stability of the compositions was confirmed for up to 5 months at 4° C. and 60 days at room temperature (20-25° C.) considering an acceptance criterion of 90-110% of temozolomide content vs the theoretical value. Based on published data, this good long-term stability could not be expected. Indeed, Trissel et al. have reported good stability of hospital-compounded suspension (10 mg/ml temozolomide; see Table 1) for 60 days at 4° C. but only up to 14 days at 23° C. Ambados et al. have reported even worse stability for an essentially similar hospital-compounded suspension (10 mg/ml temozolomide; see Table 1). They demonstrated up to 22 days of stability at 4° C. and only 8 days at 23° C.

Hence, the compositions of the invention have a significant advantage with respect to their chemical stability after reconstitution over the published compositions.

3/Crystallisation of Temozolomide in the Compositions
3-1/Characterization of Temozolomide Solid State in Suspension:

An X-ray powder diffraction (XRPD) investigation was conducted to identify the solid state of temozolomide in suspension. The following samples were analysed by XRPD:

4 batches of temozolomide API manufactured by 3 manufacturers (Supplier 1, Supplier 2 and Supplier 3)
   4 compositions, i.e. compositions #8, #9, #11 and #12.

The samples were analysed by X-ray powder diffraction in transmission mode (the sample is placed between Kapton® and Polypropylene foils). It is worth noting that Kapton® exhibits a low intensity signal in the shape of a large hump around 2θ=5.5°.

Samples provided as suspensions were subjected to centrifugation for 30 s to 1 min, to allow the separation of the liquid and solid phases. After removal of the liquid phase, the wet solid phase is extracted and analysed 'as-is' by X-ray diffraction. No sample preparation was required for the temozolomide API samples.

Surprisingly and as revealed by FIGS. 1 to 4, the solid state of temozolomide in all the compositions, i.e. in suspension, corresponds to the temozolomide monohydrate. This is even more surprising and unexpected since the temozolomide API XRPD patterns matched with the polymorph Form III described in document US 2005/0187206 (i.e. temozolomide form 1 in CSD) which is temozolomide anhydrous. This change in solid state form of temozolomide clearly indicates an in-situ conversion of temozolomide from the anhydrous form to the monohydrate form. To the knowledge of the Applicants, the monohydrate form has only been isolated after a specific synthetic route and its in-situ spontaneous formation has never been observed in pharmaceutical compositions.

Table 8 hereunder details the main peaks of the diffractogram of temozolomide manufactured by Supplier 1 and Supplier 2 compared to the main peaks of temozolomide Form III (i.e. temozolomide anhydrous) reported in US 2005/0187206. All main peaks of temozolomide API manufactured by Supplier 1 and Supplier 2 are matching the peaks of temozolomide Form III as disclosed in US 2005/0187206.

TABLE 8

Characteristic peaks of temozolomide anhydrous (Form III or Form 1 in CSD)

| Supplier 1 UB60003 | | Supplier 2 (batch IWX140044) | | US 2005/0187206- Form III | |
|---|---|---|---|---|---|
| 2-Theta | Rel. % | 2-Theta | Rel. % | 2-Theta | Rel. % |
| 10.8 | 60 | 10.9 | 93 | 10.8 | 54 |
| 13.1 | 11 | 13.3 | 10 | 13.2 | 21 |
| 14.6 | 100 | 14.7 | 86 | 14.7 | 100 |
| 16.2 | 17 | 16.3 | 29 | 16.2 | 28 |
| 16.7 | 16 | 16.8 | 13 | 16.8 | 27 |
| 17.9 | 33 | 18.1 | 31 | 18 | 50 |
| 19.0 | 36 | 19.1 | 40 | 19.1 | 45 |
| 21.4 | 11 | 21.5 | 14 | 21.5 | 27 |
| 23.7 | 10 | 23.8 | 14 | 23.8 | 23 |
| 25.1 | 7 | 25.3 | 12 | 25.2 | 18 |
| 26.4 | 95 | 26.6 | 100 | 26.6 | 75 |
| 28.7 | 71 | 28.8 | 80 | 28.8 | 71 |
| 29.7 | 34 | 29.9 | 46 | 29.8 | 43 |
| 32.6 | 10 | 32.7 | 13 | — | — |

The comparison of XRPD patterns of all the compositions (#8, #9, #11 and #12) to the diffractogram of temozolomide monohydrate (CCDC ref 665056) clearly highlights strong similarities allowing to conclude that the solid state of temozolomide in suspension is temozolomide monohydrate (FIGS. 1 to 4).

Surprisingly, this change of solid state does not impact the chemical stability of the suspension. For instance, the temozolomide assay of compositions #8 and #9 is around 100% of initial content after 14 days (see Tables 4 and 5 above). This is quite unexpected as temozolomide quickly degrades by hydrolysis upon contact with water.

Figure 2:
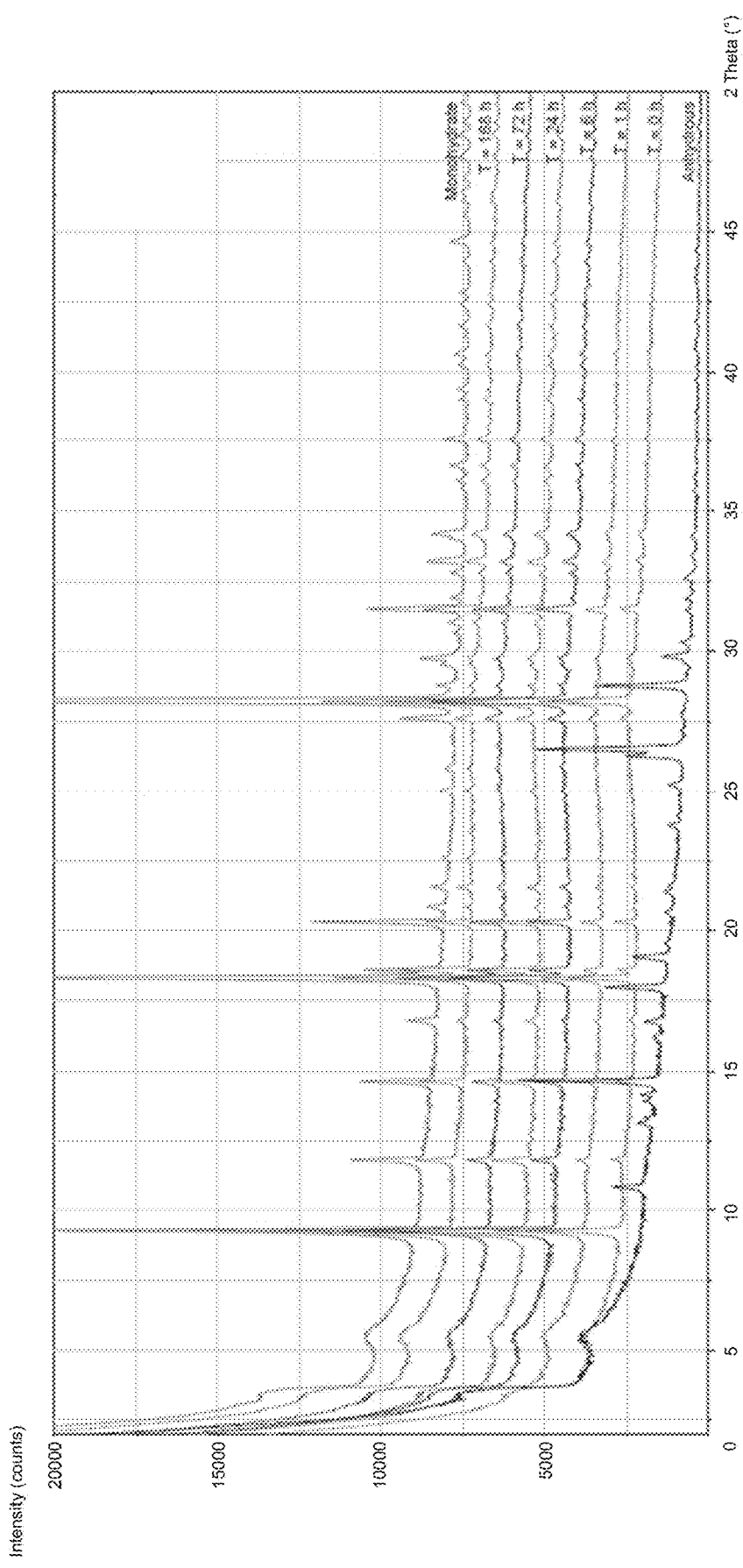
FIG. 2: XRPD diffractograms of composition #9, of anhydrous TMZ (Form III) and of TMZ monohydrate
Figure 3:
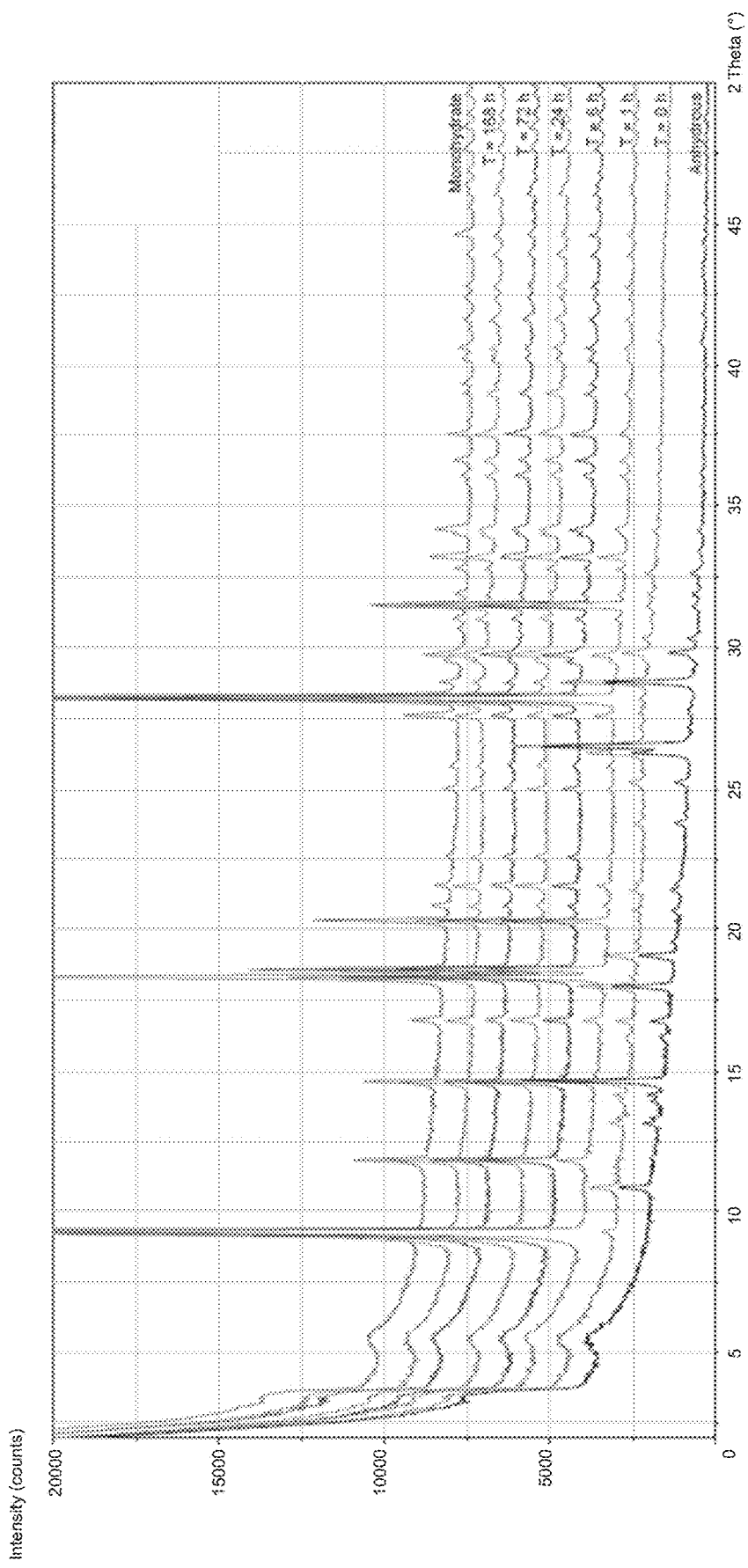
FIG. 3: XRPD diffractograms of composition #11, of anhydrous TMZ (Form III) and of TMZ monohydrate
Figure 4:
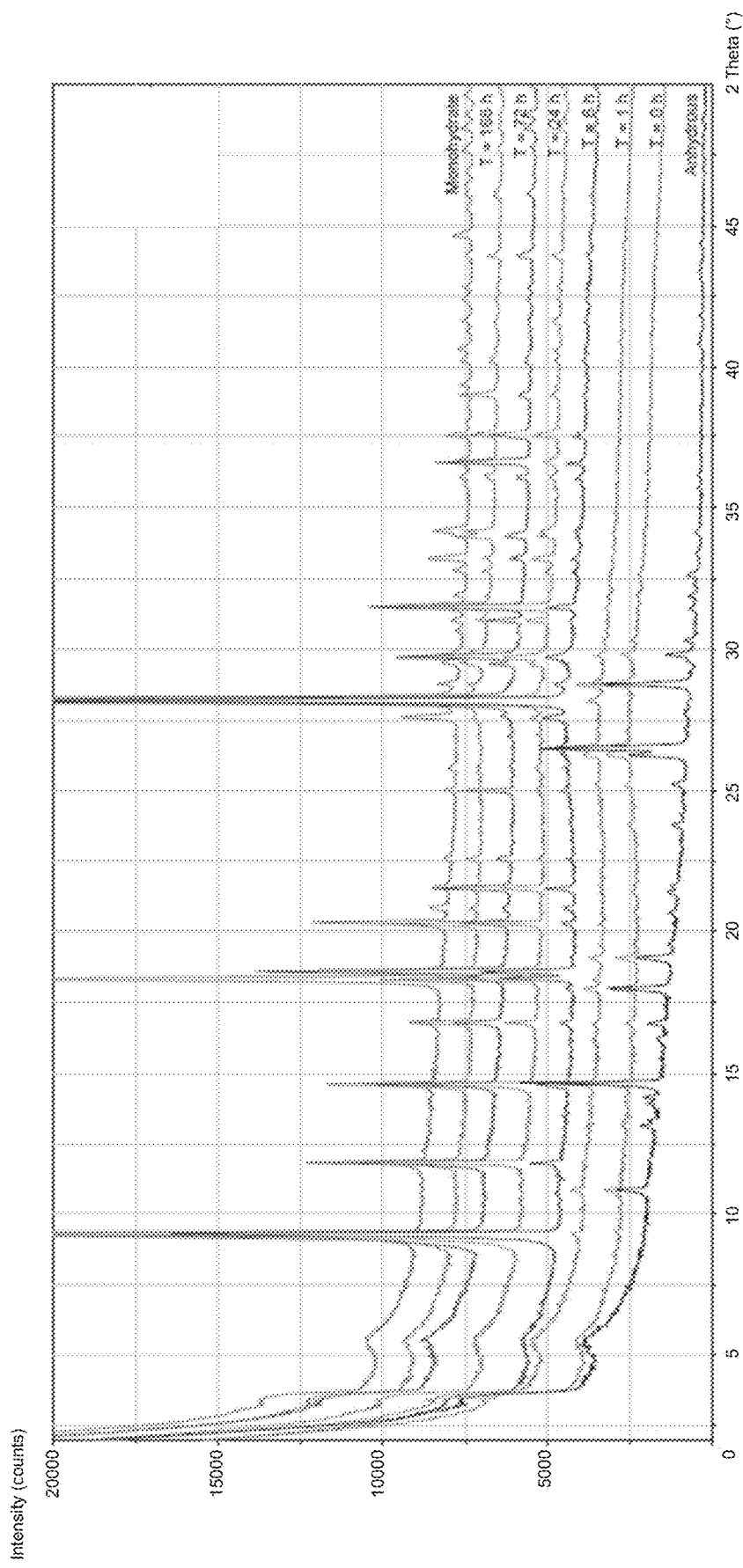
FIG. 4: XRPD diffractograms of composition #12, of anhydrous TMZ (Form III) and of TMZ monohydrate

3-2/Conversion Kinetic from Temozolomide Anhydrous into Temozolomide Monohydrate:

Furthermore, the results of these experiments shown in FIGS. 1 to 4 highlight the surprising role of silica in the suspension: see compositions #8 (FIG. 1) and #9 (FIG. 2). It triggers a rapid conversion of anhydrous temozolomide (Form III) into temozolomide monohydrate whereas this conversion takes several hours in silica-free compositions: see compositions #11 (FIG. 3) and #12 (FIG. 4).

3-3/Impact of Silica on the Homogeneity of the Suspension:

The following temozolomide suspensions were prepared. Various stirring times were applied to the suspension to evaluate the combined impact of the presence of silica and stirring time on the suspension homogeneity. The appearance of the suspension was recorded 24 h and 96 h after the preparation.

TABLE 9

Composition of various temozolomide (TMZ) suspensions (concentrations expressed in mg/ml)

| Composition # | 18 | 19 |
|---|---|---|
| TMZ Supplier 1 | 40 | 40 |
| Xanthan gum (XG) | 5 | 5 |
| Mesoporous silica | 1 | 10 |
| Citric acid | 5 | 5 |
| Sucralose | 3 | 3 |
| Cola flavour | 5 | 5 |
| Sodium benzoate | 1 | 1 |
| Water | qs | qs |

Three fractions of each formulation were prepared and stirred using a magnetic barrel for 1, 5 and 15 minutes respectively. The appearance of the suspensions was evaluated 24 h and 96 h after the preparation. The appearance of the suspensions is detailed in the table 10.

TABLE 10

Appearance of suspensions after various stirring times

| | | 1 minute | 5 minutes | 15 minutes |
|---|---|---|---|---|
| Composition 18 | 24 h | NC | NC | C |
| | 96 h | NC | NC | C |
| Composition 19 | 24 h | C | C | C |
| | 96 h | NC | C | C |

Results provided in Table 10 show that addition of mesoporous silica at 10 mg/ml allows obtaining a homogeneous suspension after a very short stirring time, as short as 5 minutes. Since the homogeneity of the suspension is linked to the particle size of temozolomide in the suspension, presence of mesoporous silica in the suspension promotes the formation of smaller temozolomide crystals and consequently enhances the homogeneity of the suspension.

4/Macroscopic and Microscopic Evaluations of the Compositions

Compositions #8, #9, #11 and #12 were analysed 24 h to 48 h after reconstitution with respect to their macroscopic appearance and using microscopic under polarized light.

Figure 5A:
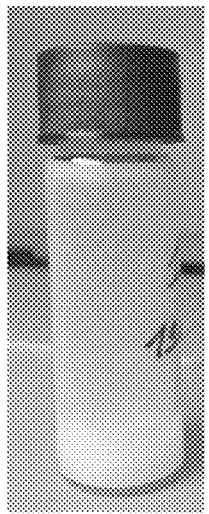
FIG. 5: Macroscopic (A) and microscopic (B) evaluation of composition #8
Figure 6A:
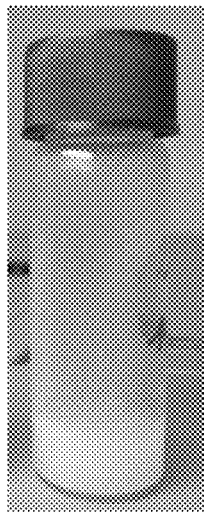
FIG. 6: Macroscopic (A) and microscopic (B) evaluation of composition #9

Compositions #8 [FIG. 5(A)] and #9 [FIG. 6(A)] exhibited a homogeneous white suspension appearance whereas the compositions #11 [FIG. 7(A)] and #12 [FIG. 8(A)], which do not contain mesoporous silica, exhibited translucent appearance with presence of large crystals.

Figure 5B:
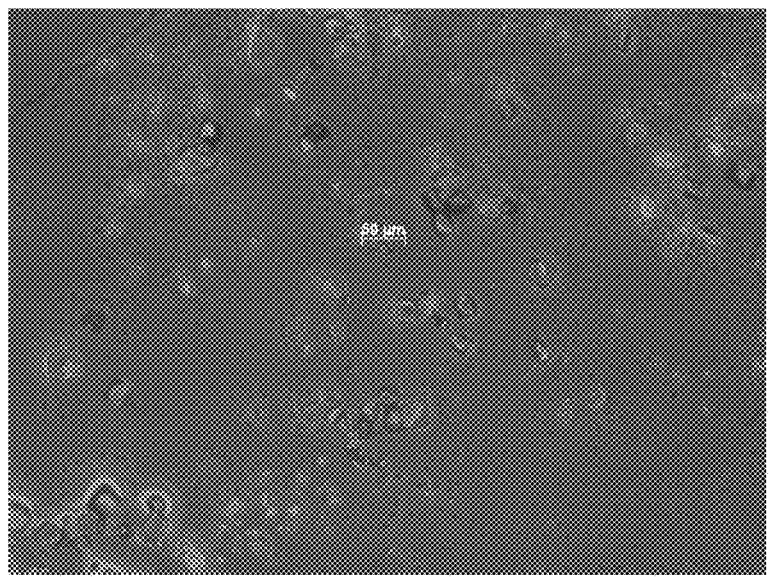
Figure 6B:
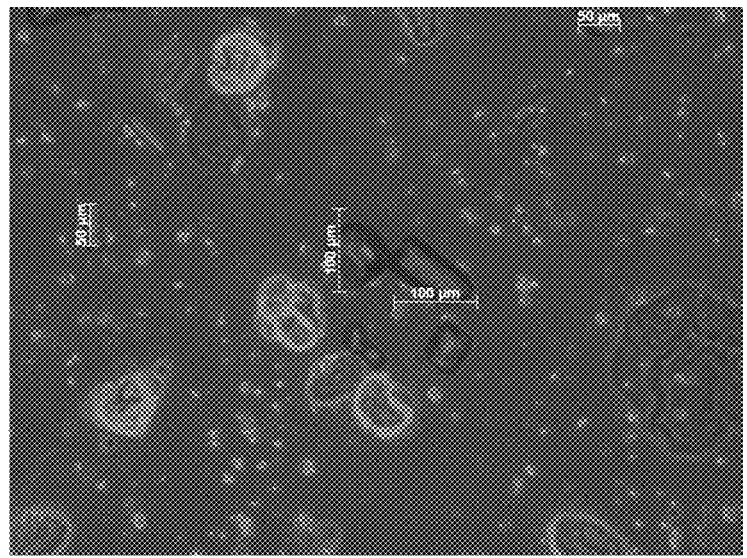

The macroscopic appearance was confirmed by microscopic evaluations. Small crystals (typically ranging from 10 to 100 μm) were reported for the compositions #8 [FIG. 5(B)] and #9 [FIG. 6(B)] whereas large crystals (>500 μm) were reported for the compositions #11 [FIG. 7(B)] and #12 [FIG. 8(B)].

Figure 9:
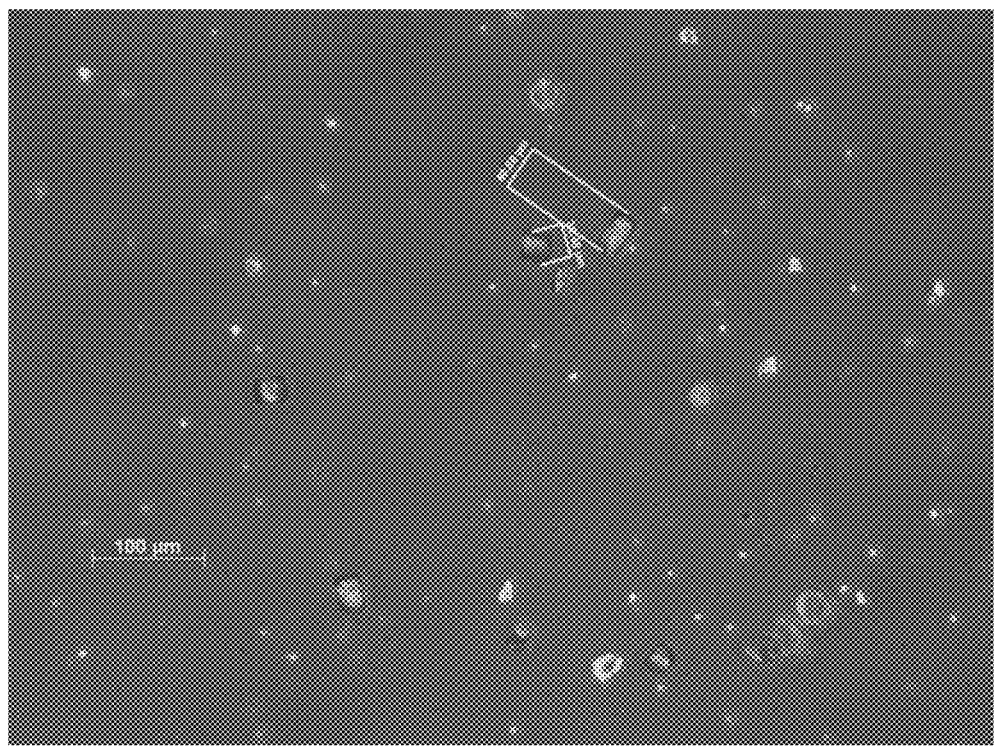
FIG. 9: Microscopic appearance of composition #8 after 28 days of storage at 4° C.
Figure 10:
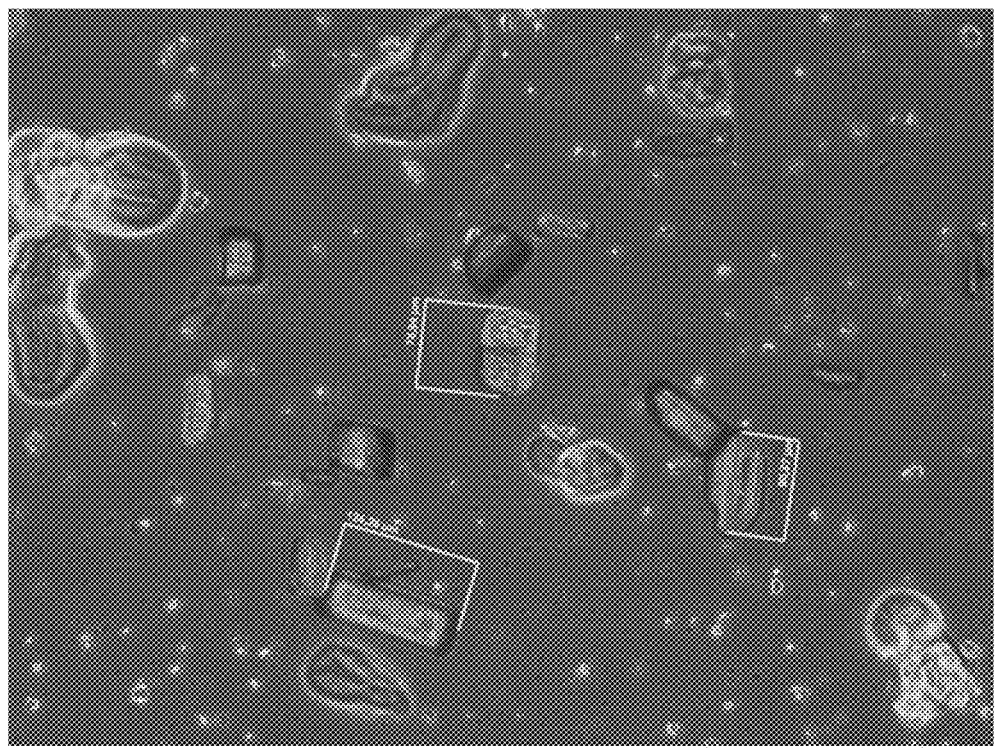
FIG. 10: Microscopic appearance of composition #9 after 28 days of storage at 4° C.

Furthermore, samples of compositions #8 (FIG. 9) and #9 (FIG. 10) were checked for microscopic appearance after 28 days of storage at 4° C. No change in the particle size could be visually reported. This confirms that presence of silica allows to control the size of temozolomide crystals in suspension and avoid formation of very large crystals.

Figure 11A:
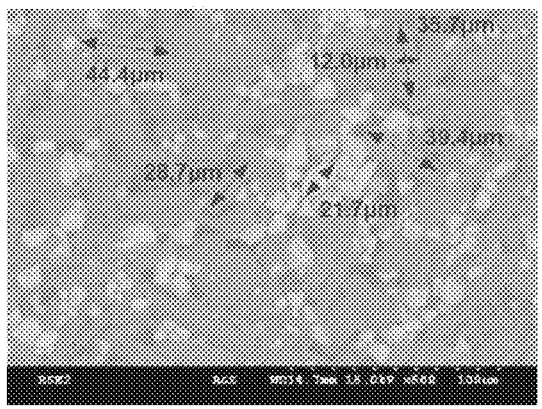
FIG. 11: Scanning Electron Microscopy (SEM) picture of composition #8 immediately (A) and 168 h after reconstitution (B)
Figure 11B:
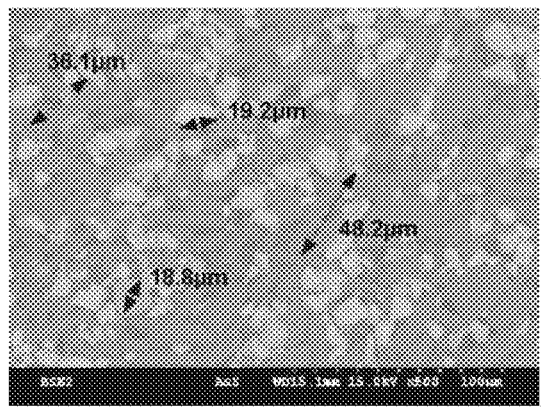
Figure 12A:
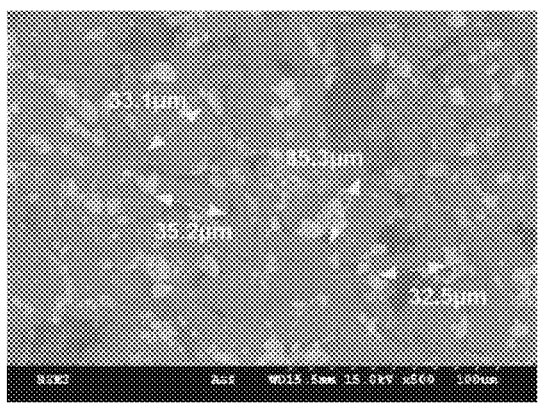
FIG. 12: Scanning Electron Microscopy (SEM) picture of composition #9 immediately (A) and 168 h after reconstitution (B)
Figure 12B:
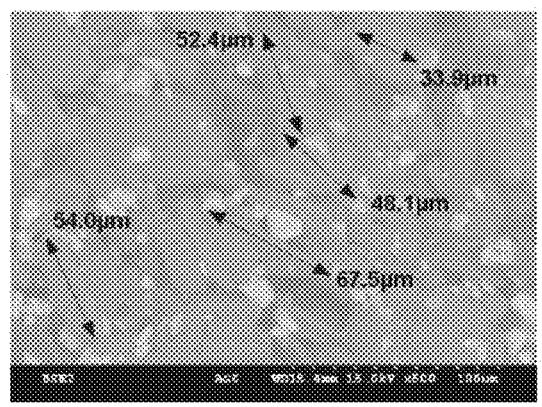
Figure 13A:
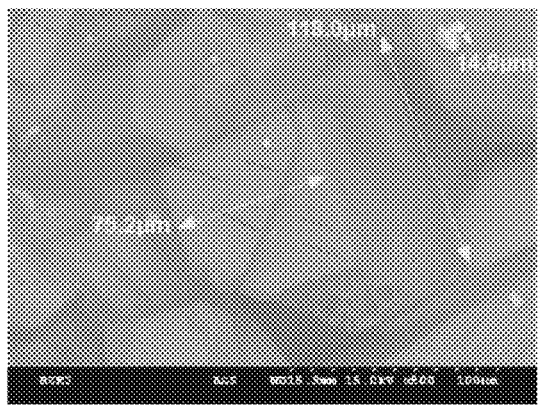
FIG. 13: Scanning Electron Microscopy (SEM) picture of composition #11 immediately (A) and 168 h after reconstitution (B)
Figure 13B:
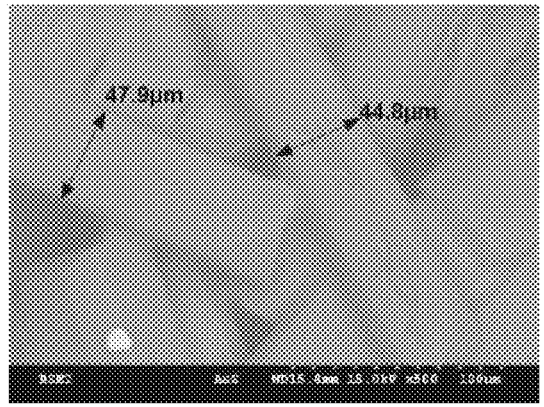
Figure 14A:
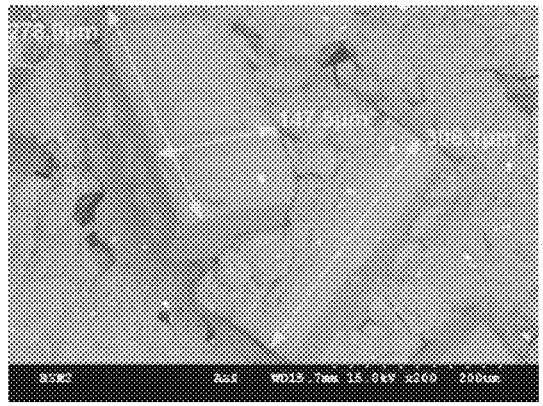
FIG. 14: Scanning Electron Microscopy (SEM) picture of composition #12 immediately (A) and 168 h after reconstitution (B)
Figure 14B:
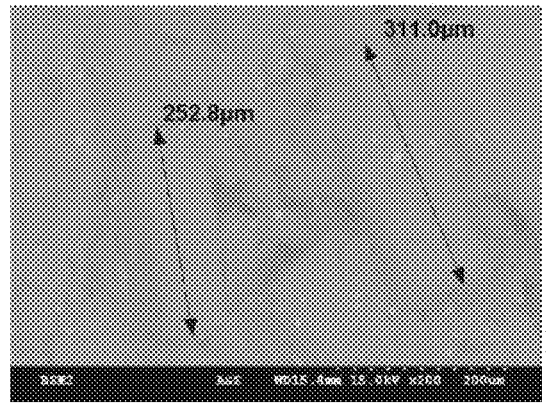

These compositions were also analysed by scanning electron microscopy (SEM) immediately and 168 h after reconstitution. SEM pictures at T0 and T168 h after reconstitution are provided in FIGS. 11 to 14. Compositions #8 (FIG. 11) and #9 (FIG. 12) exhibit small crystals which are shorter than 50 μm for the vast majority. In addition, the crystal size does not change over time. On the opposite, big crystals longer than 300 μm are observed in silica-free compositions #11 (FIG. 13) and #12 (FIG. 14). These crystals are likely to grow over time as shown in composition #11.

These SEM observations confirm the optical microscopy results and corroborate the unexpected key role of silica in controlling the recrystallisation of temozolomide monohydrate.

5/Dissolution Profile of the Compositions according to the Invention

The dissolution kinetic of the temozolomide compositions according to the invention was evaluated and compared to the dissolution kinetic of Temodal® 100 mg capsules. Dissolution test was performed with a Modular Dissolution System (Sotax) at 37° C. filled with HCl 0.01N at pH 2. Samples were withdrawn at regular time point and analysed for TMZ content by HPLC. For compositions of the invention, an equivalent dose of 250 mg was dispersed in 900 ml of dissolution medium.

Figure 15:
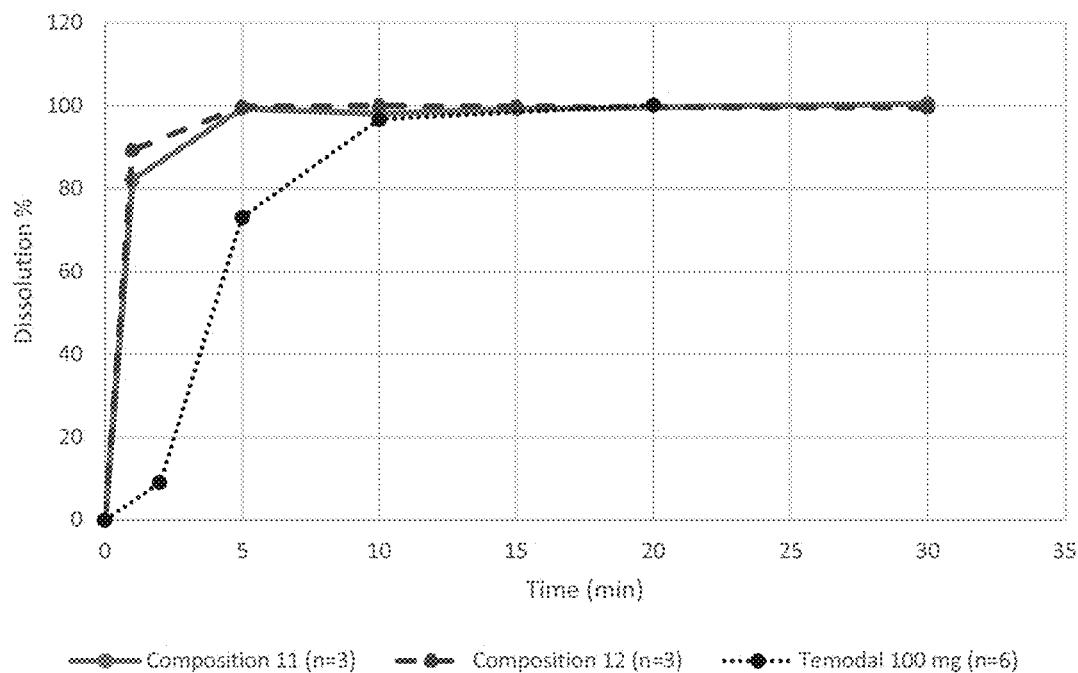
FIG. 15: Dissolution profile of compositions #8 and #9 in comparison to Temodal® 100 mg capsules

FIG. 15 displays the dissolution profiles of compositions #8 and #9 as well as that of Temodal® 100 mg capsules. Almost 100% of temozolomide dissolved within 10 minutes for all the formulations. Interestingly, compositions #8 and #9 of the invention do not show a lag time for dissolution as reported for Temodal® capsules.

What is claimed is:

1. A pharmaceutical composition in the form of an aqueous suspension comprising:
 a. temozolomide or a salt thereof;
 b. at least one agent controlling the solid state of temozolomide in the suspension;
 c. water; and
 d. optionally at least one acid in a quantity so that the pH of the composition is below 5;
 wherein:
 a concentration of temozolomide is higher than 10 mg/ml; and
 the agent controlling the solid state of temozolomide in the suspension is a compound selected from the group consisting of silica (silicon dioxide), colloidal silica, hydrophobic colloidal silica, fumed silica, and mesoporous silica,
 and wherein an amount of said agent controlling the solid state of temozolomide in the suspension is between 0.05 and 10% w/v of the composition.

2. The pharmaceutical composition according to claim 1, wherein the concentration of temozolomide ranges from 20 mg/ml to 50 mg/ml.

3. The pharmaceutical composition according to claim 1, wherein the agent controlling the solid state of temozolomide in the suspension is mesoporous silica.

4. The pharmaceutical composition according to claim 1, wherein the particle size distribution of temozolomide particles in the suspension exhibits a d90 value below 500 μm.

5. The pharmaceutical composition according to claim 1, wherein the composition further comprises at least one compound selected from the group consisting of cellulose or a derivative thereof, cyclodextrins, starch or a derivative thereof, polysaccharide-based natural gums, polyvinylpyrrolidone (PVP), poloxamers, and carbomers.

6. The pharmaceutical composition according to claim 1, further comprising said at least one acid, wherein said at least one acid is an organic acid selected from the group consisting of citric acid, tartaric acid, malic acid, maleic acid, fumaric acid, succinic acid, lactic acid, and pentetic acid.

7. The pharmaceutical composition according to claim 1, further comprising said at least one acid, wherein said at least one acid is an inorganic acid selected from the group consisting of hydrochloric acid, sulfuric acid, and phosphoric acid.

8. The pharmaceutical composition according to claim 1, wherein the pH of the composition is equal to or lower than 4.5.

9. The pharmaceutical composition according to claim 1, further comprising a flavouring agent.

10. The pharmaceutical composition according to claim 1, for administration by gastric route.

11. A method of treating cancer comprising administering the pharmaceutical composition according to claim 1.

12. The method according to claim 11, wherein the cancer is a glioma, glioblastoma multiform, anaplastic astrocytoma, neuroblastoma or Ewing's sarcoma.

13. A method for preparing a pharmaceutical composition according to claim h the method comprising mixing in a reactor or a vessel:
  temozolomide or a salt thereof;
  said at least one agent controlling the solid state of temozolomide in the suspension;
  water; and
  optionally at least one acid in a quantity so that the pH of the composition is below 5.

14. The pharmaceutical composition according to claim 5, wherein said cellulose derivative is selected from the consisting of microcrystalline cellulose, methylcellulose, ethylcellulose, hydroxymethylcellulose, hydroxyethylcellulose, hydroxypropylcellulose, hydroxypropylmethylcellulose, hydroxyethylmethyl-cellulose, and carboxymethylcellulose.

15. The pharmaceutical composition according to claim 5, wherein said starch derivative is sodium starch glycolate (SSG).

16. The pharmaceutical composition according to claim 5, wherein said polysaccharide-based natural gum is selected from the group consisting of xanthan gum, tragacanth and guar gum.

* * * * *